(12) United States Patent
Zupancic et al.

(10) Patent No.: US 7,943,779 B2
(45) Date of Patent: May 17, 2011

(54) PROCESS FOR THE PREPARATION OF OLMESARTAN MEDOXOMIL

(75) Inventors: Silvo Zupancic, Novo Mesto (SI); Anica Pecavar, Novo Mesto (SI); Miha Vrbinc, Novo Mesto (SI); Renata Osolnik, Straza (SI)

(73) Assignee: KRKA, Novo Mesto (SI)

( * ) Notice: Subject to any disclaimer, the term of this patent is extended or adjusted under 35 U.S.C. 154(b) by 137 days.

(21) Appl. No.: 11/997,133

(22) PCT Filed: Jul. 27, 2006

(86) PCT No.: PCT/EP2006/007453
§ 371 (c)(1),
(2), (4) Date: Dec. 10, 2008

(87) PCT Pub. No.: WO2007/017135
PCT Pub. Date: Feb. 15, 2007

(65) Prior Publication Data
US 2009/0131680 A1   May 21, 2009

(30) Foreign Application Priority Data

Jul. 29, 2005 (SI) .................. P 200500221
Feb. 6, 2006 (EP) ..................... 06002388

(51) Int. Cl.
*C07D 233/90* (2006.01)

(52) U.S. Cl. ...................................... 548/250; 548/253

(58) Field of Classification Search .................. 548/250, 548/253
See application file for complete search history.

(56) References Cited

U.S. PATENT DOCUMENTS

2005/0119488 A1   6/2005   Razzetti et al.

FOREIGN PATENT DOCUMENTS

| EP | 0503785 A1 * | 9/1992 |
| EP | 0668272 A2 | 8/1995 |
| WO | WO 2006/029056 A1 | 3/2006 |

OTHER PUBLICATIONS

Koike et al. 2003 Annual Report of Sankyo Research Laboratories 55:1-89.
Yanagisawa et al. 1996 "Nonpeptide Angiotensin II Receptor Antagonists: Synthesis, Biological Activities, and Structure-Activity Relationships of Imidazole-5-carboxylic Acids Bearing Alkyl, Alkenyl, and Hydroxyalkyl Substituents at the 4-Position and Their Related Compounds" *Journal of Medicinal Chemistry* 39(1):323-338.

* cited by examiner

*Primary Examiner* — Susannah Chung
(74) *Attorney, Agent, or Firm* — Knobbe Martens Olson & Bear LLP

(57) ABSTRACT

The present invention relates to an improved process for the manufacture of olmesartan and pharmaceutically acceptable salts and esters thereof as an active ingredient of a medicament for the treatment of hypertension and related diseases and conditions.

18 Claims, 1 Drawing Sheet

PROCESS FOR THE PREPARATION OF OLMESARTAN MEDOXOMIL

RELATED APPLICATIONS

This application is a U.S. National Phase of International Application No. PCT/EP2006/007453, filed 27 Jul. 2006, designating the U.S. and published in English 15 Feb. 2007 as WO 2007/017135, which claims the benefit of European application No. 06002388.4, filed 6 Feb. 2006 and SI application No. P 200500221, filed 29 Jul. 2005.

FIELD OF THE INVENTION

The present invention relates to an improved process for the manufacture of olmesartan and to pharmaceutically acceptable salts and esters thereof, as active ingredients of a medicament for the treatment of hypertension and related diseases and conditions.

TECHNICAL PROBLEM

In medicine olmesartan medoxomil, chemically described as (5-methyl-2-oxo-1,3-dioxolen-4-yl)methyl-4-(1-hydroxy-1-methylethyl)-2-propyl-1-{4-[2-(tetrazol-5-yl)phenyl]phenyl}methylimidazole-5-carboxylate, is widely used for the treatment of hypertension and related diseases and conditions due to its ability to inhibit the angiotensin-converting enzyme. As an angiotensin II receptor antagonist, olmesartan medoxomil avoids the side-effects of calcium antagonists, shows high stability and obvious curative effects.

BACKGROUND OF THE INVENTION

In EP 0 503 785 B1 processes for the preparation of olmesartan medoxomil is disclosed involving inter alia reacting (5-methyl-2-oxo-1,3-dioxolen-4-yl)methyl-4-(1-hydroxy-1-methylethyl)-2-propylimidazole-5-carboxylate and 4-[2-trityltetrazol-5-yl)phenyl]benzyl bromide in N,N-dimethyl acetamide in the presence of potassium carbonate, or reacting ethyl-4-(1-hydroxy-1-methylethyl)-2-propylimidazole-5-carboxylate and 4-[2-trityltetrazol-5-yl)phenyl]benzyl bromide in N,N-dimethylformamide in the presence of sodium hydride. In example 70 the alkylation of ethyl-4-/1-hydroxy-1-methylethyl)-2-propylimidazole-5-carboxylate with 4'-bromomethylbiphenyl-2-carbonitrile in N,N-dimethyl acetamide and in the presence of potassium t-butoxide is disclosed. Common to all the processes disclosed is that the alkylated product is subjected to a column chromatography in order to obtain an acceptable purity. For the preparation of an ester, the product obtained is described to be hydrolyzed by means of an alkali metal hydroxide, the salt is isolated and further esterified. In the last step, the trityl protection group is removed by reacting the trityl medoxomil ester in acetic acid.

In J. Med. Chem., 39 (1996), 323-338 the alkylation step between 4-[2-trityltetrazol-5-yl)-phenyl]benzyl bromide or its analogues and the imidazole intermediate is described to have been performed in N,N-dimethyl acetamide and in the presence of potassium t-butoxide. EtOAc and water is added to the reaction mixture and the product is extracted into EtOAc. The purification of the product is achieved by the use of flash column chromatography (EtOAc/hexane, 1:2) and optionally by an additional crystallization from IPE, hexane, EtOAc or mixtures thereof.

In EP 0 796 852 B1 the authors disclose a safer and easier preparation of 5-substituted tetrazoles without the use of Bu$_3$SnN$_3$. The process comprises reacting a nitrile with an inorganic azide salt in an aromatic hydrocarbon solvent in the presence of an amine salt.

In WO 2004/085428 there is described a new process for the preparation of olmesartan medoxomil. In the process the ring in 4,4-dimethyl-2-propyl-1-{4-[2-(triphenyl-methyl-tert-azole-5-yl)phenyl]phenyl}methyl-4,6-dihydrofuran[3,4d]imidazole-6-one is opened, and the resulting 4-(1-hydroxy-1-methylethyl)-2-propyl-1-{4-[2-(triphenyl-methyl-tert-azole-5yl)-phenyl]phenyl}methylimidazole-5-carboxylic acid is subsequently condensated with 4-bromo (or chloro)methyl-5-methyl-2-oxy-1,3-dioxyheterocyclopentene under the action of alkali. After deprotection of the triphenylmethyl protective group, olmesartan medoxomil is obtained.

WO 2004/083213 relates to compounds represented by the following formula (II) and their pharmaceutically acceptable salts, and to a process for their preparation. They are used as intermediates for the preparation of angiotensin II receptor antagonist, e.g. olmesartan medoxomil.

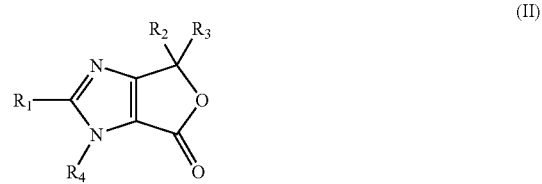

(II)

A general shortcomings of the prior art methods resides in that processes proposed involve, apart from applying column chromatography, additional isolation steps, which are acknowledged to decrease yield and rendering any process cumbersome. Also the use of some solvents, such as acetic acid, in late reaction steps require additional crystallization/purification steps, since especially acetic acid is known to potentially lead to the formation of persistent impurities during the drying process and is also difficult to remove from the pharmaceutically active compound when present as a residual solvent.

In view of the shortcoming of the prior art an object of the present invention resides in providing an alternative process for obtaining olmesartan medoxomil, which may be rapidly carried out, is economical and provides the desired compound in high purity.

SUMMARY OF THE INVENTION

The above problem has been solved by providing an improved synthesis method for the manufacture of olmesartan and pharmaceutically acceptable salts and esters which comprises the step of alkylating ethyl 4-(1-hydroxy-1-methylethyl)-2-propylimidazole-5-carboxylate (III) with 4-[2-(trityltetrazol-5-yl)phenyl]-benzyl bromide (IVa) or 4'-bromomethylbiphenyl-2-carbonitrile (IVb) in an organic solvent and in the presence of a base, wherein as a solvent acetonitrile is utilized for both, the reaction solvent and the crystallization solvent.

According to a first embodiment the present invention relates to an improved synthesis method for the manufacture of olmesartan medoxomil which comprises:

the step of alkylating ethyl 4-(1-hydroxy-1-methylethyl)-2-propylimidazole-5-carboxylate (III) with 4-[2-(trityltetrazol-5-yl)phenyl]-benzyl bromide (IVa) in an organic solvent and in the presence of a base, wherein the same solvent is used as the reaction solvent and as the crystallization solvent, and a one-pot process, comprised of the hydrolysis of the ethyl ester V, the esterification with a 4-substituted methyl-5-methyl-2-oxo-1,3-dioxolene derivative (VI), and the subsequent deprotection of the trityl protection group without any isolation steps during the process.

According to a second embodiment the present invention relates to an improved synthesis for the manufacture of olmesartan medoxomil which comprises:

the step of alkylating ethyl 4-(1-hydroxy-1-methylethyl)-2-propylimidazole-5-carboxylate (III) with 4'-bromomethylbiphenyl-2-carbonitrile (IVb) in an organic solvent and in the presence of a base, wherein the same solvent is used as the reaction solvent and as the crystallization solvent, and a process, comprised of the hydrolysis of the ethyl ester, the esterification with a 4-substituted methyl-5-methyl-2-oxo-1,3-dioxolene derivative (VI), and the subsequent cycloaddition reaction of the cyano moiety into the tetrazole group.

It has unexpectedly been found that in the preparation of olmesartan medoxomil the alkylation step leads to much higher yields and lower level of impurities if performed in acetonitrile as the solvent and in the presence of a base, selected e.g. from carbonates or hydroxides, such as potassium carbonate, sodium carbonate, potassium hydroxide, sodium hydroxide and lithium hydroxide, instead of using N,N-dimethylformamide as a solvent known in the prior art. In addition, acetonitrile proved to be perfectly suitable as a crystallization solvent as well, so that extraction with a second, different solvent, which is immiscible with water, may be omitted as well as a purification of the product by column chromatography. Especially the feature of acetonitrile also being suitable to serve as a crystallization medium renders the process highly advantageous for industrial production, since column chromatography purification is rarely applicable on industrial scale.

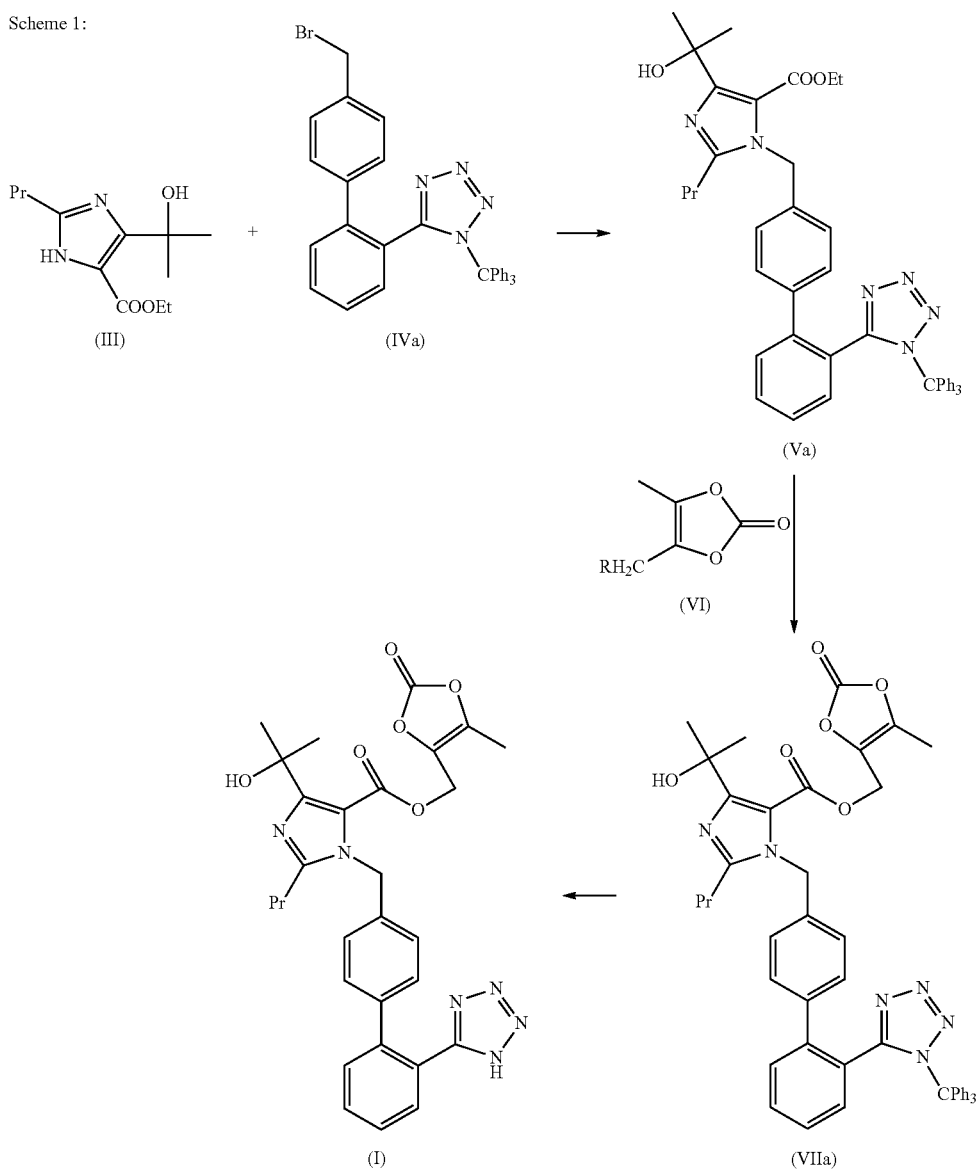

Scheme 1:

When the alkylation step is performed with 4'-bromomethylbiphenyl-2-carbonitrile (IVb), the deprotection of the trityl protection group is replaced by a cycloaddition reaction and may also be performed before hydrolysis of the ethyl ester and the esterification with a 4-substituted methyl-5-methyl-2-oxo-1,3-dioxolene derivative (VI). The cycloaddition reaction towards the tetrazole moiety may be carried out following any procedure known from prior art, e.g. by the use of $Bu_3SnN_3$, $NaN_3/ZnCl_2$, or as described in EP 0 796 852 B1. Optionally, the trityl protection group or any other suitable protection group known to the person skilled in the art may also be used in order to achieve purification.

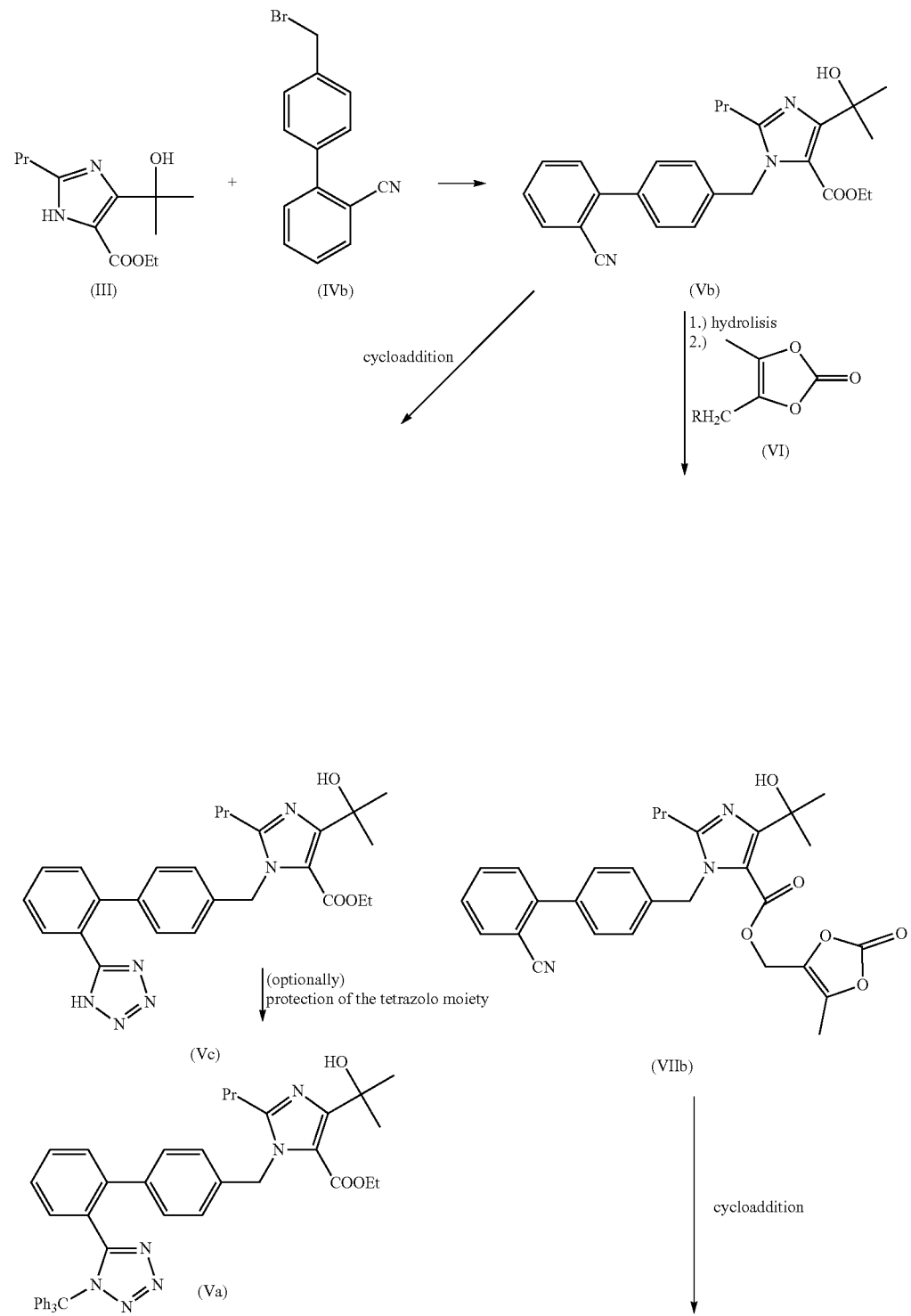

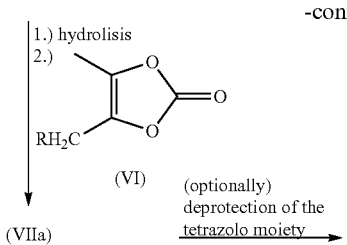
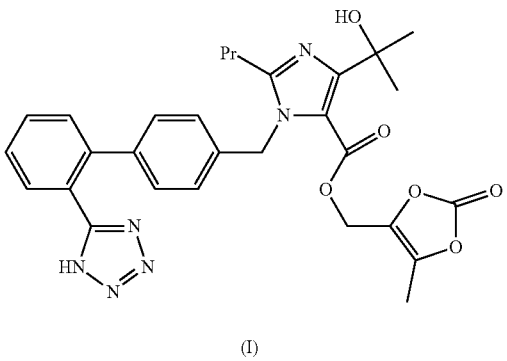

-continued (I)

In a further aspect, the present invention also provides an improved process for the preparation of a pharmaceutical formulation containing highly pure olmesartan medoxomil, exhibiting a (HPLC) purity of over 99.5%, preferably over 99.6%, more preferably 99.7%, even more preferably 99.8% and most preferred 99.9%, and with individual impurities under 0.1% (all by weight).

In a further aspect, the present invention provides olmesartan medoxomil substantially free of dehydro and N-alkylated impurities of the structural formulas

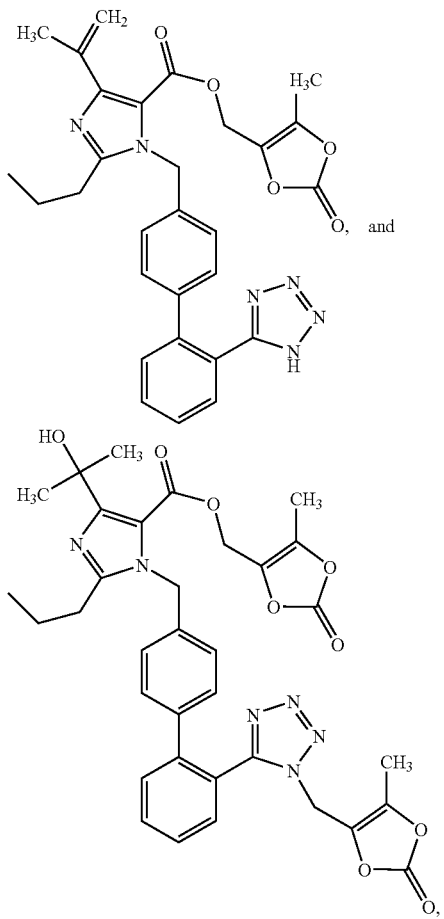

respectively.

In the following, preferred embodiments of the invention are described.

DETAILED DESCRIPTION OF THE INVENTION

Figure 1:
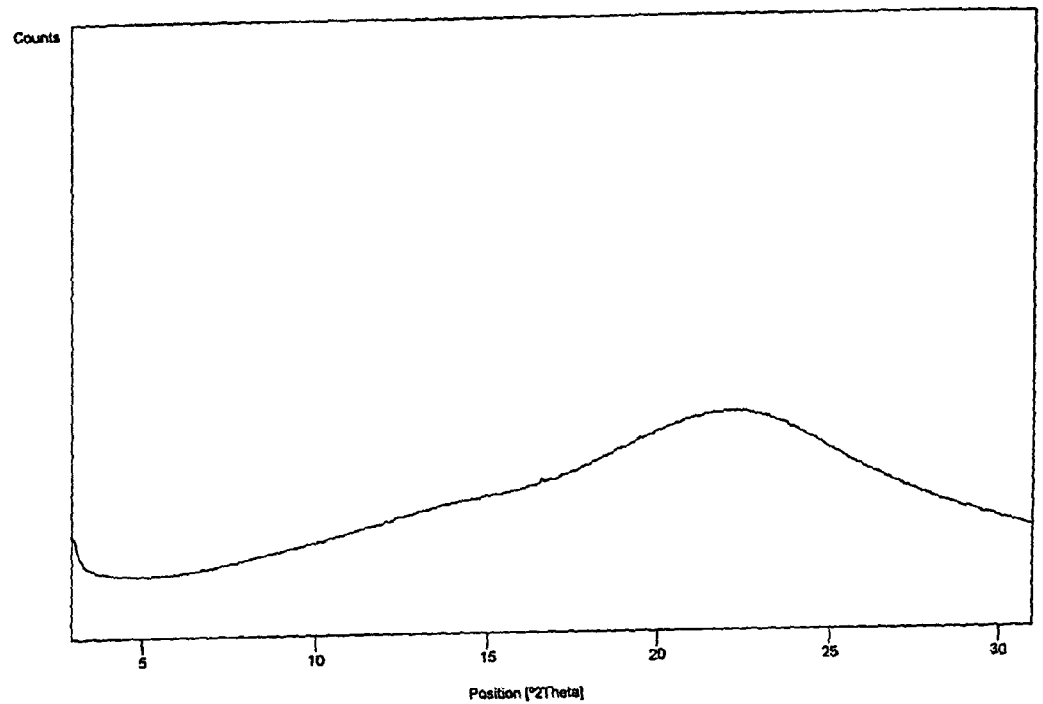
FIG. 1 represents a typical X-ray powder diffractogram of amorphous olmesartan medoxomile.

The present invention relates to an improved synthesis for the manufacture of olmesartan medoxomil which comprises the alkylation of ethyl 4-(1-hydroxy-1-methylethyl)-2-propyl-imidazole-5-carboxylate (III) with 4-[2-(trityltetrazol-5-yl)phenyl]-benzyl bromide (IVa) or 4'-bromomethylbiphenyl-2-carbonitrile (IVb) in an organic solvent, and in the presence of a base, wherein the same solvent, acetonitrile, is used as the reaction solvent and as the crystallization solvent.

In a second aspect of the present invention a one-pot process which follows the alkylation step, comprised of the hydrolysis of the ethyl ester (Va), the esterification with a 4-substituted methyl-5-methyl-2-oxo-1,3-dioxolene derivative, and the subsequent deprotection of the trityl protection group without any isolation steps during the process is disclosed. If the alkylation reaction is carried out with 4'-bromomethylbiphenyl-2-carbonitrile (IVb), the second aspect of the present invention includes a process, comprised of the hydrolysis of the ethyl ester, the esterification with a 4-substituted methyl-5-methyl-2-oxo-1,3-dioxolene derivative (VI), and the subsequent cycloaddition reaction of the cyano moiety into the tetrazole group.

The first embodiment of the present invention relates to an improved synthesis for the manufacture of olmesartan medoxomil which comprises:
i. the alkylation step of ethyl 4-(1-hydroxy-1-methylethyl)-2-propylimidazole-5-carboxylate (III) with 4-[2-(trityltetrazol-5-yl)phenyl]-benzyl bromide (IVa) in an organic solvent, and in the presence of a base, wherein the same solvent is used as the reaction solvent and as the crystallization solvent, and
ii. a one-pot process, comprised of the hydrolysis of the ethyl ester, the esterification with a 4-substituted methyl-5-methyl-2-oxo-1,3-dioxolene derivative (VI), and the subsequent deprotection of the trityl protection group without any isolations during the process.

The second embodiment of the present invention relates to an improved synthesis for the manufacture of olmesartan medoxomil which comprises:
the alkylation step of ethyl 4-(1-hydroxy-1-methylethyl)-2-propylimidazole-5-carboxylate (III) with 4'-bromomethylbiphenyl-2-carbonitrile (IVb) in an organic solvent and in the presence of a base, wherein the same solvent is used as the reaction solvent and as the crystallization solvent, and a process, comprised of the hydrolysis of the ethyl ester, the esterification with a 4-substituted methyl-5-methyl-2-oxo-1,3-dioxolene derivative (VI), and the subsequent cycloaddition reaction of the cyano moiety into the tetrazole group.

When the alkylation step is performed with 4'-bromomethylbiphenyl-2-carbonitrile (IVb), the deprotection of the trityl protection group is replaced by a cycloaddition reaction and may also be performed before the hydrolysis of the ethyl ester and the esterification with a 4-substituted methyl-5-methyl-2-oxo-1,3-dioxolene derivative (VI).

Optionally, after the alkylation step of ethyl 4-(1-hydroxy-1-methylethyl)-2-propylimidazole-5-carboxylate (III) with 4-[2-(trityltetrazol-5-yl)phenyl]-benzyl bromide (IVa) or 4'-bromomethylbiphenyl-2-carbonitrile (IVb) is completed, the organic solvent is partially evaporated in order to facilitate the crystallization of the product. If needed, the alkylated product (Va-c) may also be suspended in water and recrystallized from the same solvent as used in the alkylation reaction.

In the preferred embodiment, the present invention relates to an improved synthesis for the manufacture of olmesartan medoxomil which comprises:

i. the alkylation step of ethyl 4-(1-hydroxy-1-methylethyl)-2-propylimidazole-5-carboxylate (III) with 4-[2-(trityltetrazol-5-yl)phenyl]-benzyl bromide (IVa) in acetonitrile and in the presence of potassium carbonate as base, to yield compound Va, wherein acetonitrile is used as the reaction solvent and as the crystallization solvent, and ii. a one-pot process, comprised of the hydrolysis of the ethyl ester, the esterification with a 4-substituted methyl-5-methyl-2-oxo-1,3-dioxolene derivative (VI), preferably 4-chloromethyl-5-methyl-2-oxo-1,3-dioxolene, and the subsequent deprotection of the trityl protection group without any isolations during the process, wherein the deprotection of the trityl protection group is carried out in EtOAc and in the presence of HCl and a co-solvent.

Optionally, after the alkylation reaction is completed, acetonitrile is partially evaporated in order to facilitate crystallization of the product (Va). If needed, the product may also be suspended in water and recrystallized from acetonitrile.

Surprisingly, the use of the same organic solvent, acetonitrile, as the reaction and the crystallization solvent during the alkylation reaction between 4-(1-hydroxy-1-methylethyl)-2-propylimidazole-5-carboxylate (III) with 4-[2-(trityltetrazol-5-yl)phenyl]-benzyl bromide (IVa) led to much higher yields (88%) and lower level of impurities despite the fact that the extraction step with a second solvent which is immiscible with water is omitted, as well as purification of the product by column chromatography. The products, ethyl 4-(1-hydroxy-1-methylethyl)-2-propyl-1-{4-[2-(tritylterazol-5-yl)phenyl]phenyl}-methyl-imidazole-5-carboxylate (Va) and ethyl 4-(1-hydroxy-1-methylethyl)-2-propyl-1-{4-[2-cyanobiphenyl}methyl imidazole-5-carboxylate (Vb), are isolated by crystallization. Optionally, the reaction mixture is concentrated to approximately ⅓ of the original volume and cooled to a temperature below 25° C. After the precipitated product is filtered, it is suspended in water to remove excess of inorganic base. The product may be recrystallized from an organic solvent, for example from acetonitrile.

In the second aspect of the invention, a one-pot process which follows the alkylation step, comprised of the hydrolysis of the ethyl ester, the esterification with a 4-substituted methyl-5-methyl-2-oxo-1,3-dioxolene derivative, and the subsequent deprotection of the trityl protection group without any isolations during the process is disclosed. The 4-substituted methyl-5-methyl-2-oxo-1,3-dioxolene derivative (VI) is a compound, wherein R represents a good leaving group, e.g. a halogen such as Cl, Br, and I, p-toluenesulfonyloxy (tosylate), p-bromobenzenesulfonyloxy (brosylate), p-nitrobenzenesulfonyloxy (nosylate) or methylsulfonyloxy (mesylate) group. In the preferred embodiment, 4-chloromethyl-5-methyl-2-oxo-1,3-dioxolene is used.

Ethyl-4-(1-hydroxy-1-methylethyl)-2-propyl-1-{4-[2-(trityltetrazol-5-yl)phenyl]phenyl}-methyl-imidazole-5-carboxylate (Va) is dissolved in an appropriate solvent and the first base is added and the reaction mixture is stirred for 24 hours, preferably for 4 to 12 hours, at a temperature between 15° C. and 30° C., preferably at ambient temperature.

After hydrolysis of the ethyl moiety is completed, the 4-substituted methyl-5-methyl-2-oxo-1,3-dioxolene derivative, preferably 4-chloromethyl-5-methyl-2-oxo-1,3-dioxolene, may simply be added to the reaction mixture, together with a second base, without previous isolation of the resulting salt. Before addition, the mixture is cooled, preferably to a temperature of to or below 10° C. more preferably to or below 5° C., and both reagents are added at the selected temperature. The reaction mixture is heated for up to 5 hours, preferably for 2 hours, at a temperature between room temperature and 100° C., preferably at a temperature between 20 and 70° C., more preferably between 30 and 40° C.

As solvents for the hydrolysis and esterification step, N,N-dimethyl acetamide, other amide solvents, nitrites or any other polar and water miscible solvent may be used. In the preferred embodiment the solvent is DMA.

As first bases alkali metal hydroxides, metal alcoxides or carbonates are used, in an amount of 1 to 1.5 equivalents. In the preferred embodiment sodium hydroxide is used as the first base.

As second bases alkali or earth alkali metal hydroxides, metal alcoxides or carbonates are used, in an amount of 0.5 to 1.5 equivalents. In the preferred embodiment potassium carbonate is used as the second base.

In a preferred embodiment, the present invention provides olmesartan medoxomil substantially free of dehydro and N alkylated impurities. This invention also provides a method of synthesizing olmesatan medoxomil that comprises an amount of dehydro and N alkylated impurities not greater than 0.2%, preferably not greater than 0.10%, which comprises:

analyzing and selecting commercial bathes of the 4-substituted methyl-5-methyl-2-oxo-1,3-dioxolene derivative or purification of the 4-substituted methyl-5-methyl-2-oxo-1,3-dioxolene derivative and analyzing the purified product.

using batches of dioxolene derivative which have an assay of more than 90%, preferably more than 95%.

After completion of the esterification step, the reaction mixture is cooled to below 15° C., a second water immiscible solvent is added to the reaction mixture together with some brine and is extracted. Organic fractions are collected, washed with brine and dried over a desiccant, e.g. anhydrous sodium or magnesium sulfate (VI). The extractions are performed at a temperature below 25° C.

As water immiscible solvents for the extraction solvents with low solubility of olmesartan medoxomil, such as esters, ethers, halogenated hydrocarbons can be chosen. Preferably the water immiscible solvent is ethyl acetate.

In the trityl moiety deprotection step the second water immiscible solvent which was added after the esterification step may be partly evaporated, an acid, selected from organic acid, inorganic acid, their derivatives and mixtures thereof, and a co-solvent are added. The co-solvent may be chosen from alcohols, ketones, nitrites or water. The concentration of the co-solvent is up to 30% (v/v), preferably up to 20% (v/v). Preferably, the co-solvent is MeOH or EtOH. As solvents for the trityl moiety deprotection step, the same solvents are used as for the extraction step mentioned above. Preferably the solvent for the trityl moiety deprotection step is ethyl acetate.

The reaction mixture is heated to a temperature of between 15 and 30° C., preferably the reaction is performed at room temperature, for up to 5 hours, preferably for 3 hours.

The acid may be chosen among HCl, HBr, HI, $H_2SO_4$, $H_3PO_4$ or other suitable inorganic acids. Preferably, HCl as a solution in water or in an organic solvent or in gaseous form is added.

After the deprotection process being completed, the reaction mixture is cooled, preferably to room temperature, and neutralized with a solution of an inorganic base to pH value up to 6 preferably to a pH value between 3 and 5. The phases are separated and the water phase may be re-extracted with an organic solvent. The collected organic phases are dried, filtered and concentrated. The mixture is cooled and the product precipitates. The final product (I) is filtered and washed with fresh organic solvent and the by-product of the reaction (trityl alcohol), remains completely dissolved in the filtrate.

Suitable inorganic bases used for the neutralization are NaOH, KOH, LiOH, $Ca(OH)_2$, $Na_2CO_3$, $NaHCO_3$, $K_2CO_3$, $KHCO_3$, inorganic phosphates. Preferably a water solution of NaOH is used.

The crude product may be recrystallized from organic solvents such as: acetates, ketones, alcohols, nitrites and mixtures of them. The crystalline forms of the products crystallized from above solvents were the same as described in *Annual Report of Sankyo Research Laboratories Vol. 55* (2003). If the solution of olmesartan medoxomil is slowly crystallized from isobutanol or THF, a new form of olmesartan medoxomil is obtained which is characterized by the melting interval 182-184° C. and by an X-ray diffraction pattern with peaks at 7.4, 9.0, 9.6, 11.6, 12.0, 13.4, 16.0, 17.9, 21.1±0.2 degrees 2-theta. X-ray powder diffraction patterns were obtained by Phillips PW3040/60 X'Pert PRO powder diffractometer; CuKα radiation 1.541874 Å, 3°<2θ<31°. The phrase "slow crystallization" shall designate crystallization wherein the solution of olmesartan medoxomil is left to crystallize for more than 8 h.

During the crystallization process and during filtration, solvates of olmesartan medoxomil may form.

The amorphous form of olmesartan medoxomil is prepared, when a solution of olmesartan medoxomil in an organic solvent, such as ethers, halogenated hydrocarbons and alcohols, is evaporated, spray dried or lyophilised, and characterized by the glass transition temperature of about 120-140° C. and the X-ray powder diffractogram depicted in FIG. 1.

When olmesartan medoxomil is crystallized from organic solvents at a pH value less than 2, the salt of olmesartan medoksomil is isolated. This pH value may be achieved by adding inorganic acids such as: HCl, $H_2SO_4$, $H_3PO_4$, HBr, or strong organic acids such as $CF_3COOH$, HCOOH, $CH_3COOH$, acetic anhydride etc.

It is important to control size of particles of olmesartan medoxomil during its preparation. Average particle size of particles prepared and/or used in our work is 1 to 80 μm, preferably below 30 μm, which are usually obtained by crystallization of olmesartan medoxomil from organic solvents or their mixtures with water, while stirring. If unstirred, crystallization from organic solvents or their mixtures with water might also yield bigger particles, e.g. with an average diameter of above 100 μm which need to be milled or processed in any other way which reduces particle size, prior to their application in pharmaceutical formulations. However, it is not enough to control only the average size of particles, but also particle size distribution. The following parameters are defined to control particle size distribution:

10% of particles smaller than 20 μm, preferably smaller than 15 μm;

50% of particles smaller than 80 μm, preferably smaller than 50 μm,

90% of particles smaller than 170 μm, preferably smaller than 140 μm.

Average particle size and particle size distribution is important to assure that the technological process is suitable for being implemented on an industrial scale, i.e. does not cause segregation of ingredients of tabletting mixture if it is not tableted/compressed just after preparation of tabletting mixture.

It has surprisingly been found out that the addition of small amounts of an acid substance to the pharmaceutical formulation leading to a pH drop of at least 0.2 pH unit when compared to the pharmaceutical formulation without the acid substance inclusion, increases the dissolution profiles and improves the stability of the product as less degradation products are formed over extended periods of time. The acid substances added may be of inorganic or organic nature, e.g. acid inorganic salts such as phosphates may be applied or organic acids and/or salts thereof such as citric acid, ascorbic acid, tartaric acid, malic acid, stearic acid, palmitinic acid, lactic acid, gluconic acid, proprionic acid, amino acids etc.

The formulations of olmesartan medoxomil may be prepared by well known technological processes such as direct compression or wet granulation (with water or organic solvents, e.g. MeOH, or mixtures thereof), dry granulation or lyophilization. Preferably, direct compression process is used. Direct compression process may be performed in the way that (a) active ingredient is added to the mixture of excipients and compressed, or (b) active ingredient is mixed together with excipients and compressed.

Solid dosage form (e.g. tablet cores) can be optionally coated.

Direct compression process is performed due to low percentage of active ingredient in total weight of tablet. The term "by percentage" is meant to indicate % by weight of active ingredient in total weight of tablet. The term "low percentage of active ingredient" is meant to indicate less than 20% by weight of active ingredient in total weight of tablet.

Excipients may optionally be processed by wet granulation, using either water or organic solvent or mixture thereof as granulating liquid. By processing of excipients by wet granulation, it means homogenisation of excipients and addition of granulating liquid to the mixture thereof. Granulating liquid can optionally contain binder or binders, either individual or mixtures thereof.

Optionally, surfactants can be included in solid pharmaceutical formulation. Surfactants can be selected from the group of non-ionic or ionic surfactants or mixtures thereof.

Suitable non-ionic surfactants are selected from the group of alkylglucosides, alkylmaltosides, alkylthioglucosides, lauryl macrogolglycerides, polyoxyethylene alkylphenols, polyoxyethylene alkylethers, polyethylene glycol fatty acid esters, polyethylene glycol glycerol fatty acid esters, polyoxyethylene sorbitan fatty acid esters, polyoxyethylene-polyoxypropylene block copolymers, polyglyceryl fatty acid esters, polyoxyethylene glycerides, polyoxyethylene vegetable oils, polyoxyethylene hydrogenated vegetable oils, sterols, and mixtures thereof. Preferred non-ionic surfactants are polyoxyethylene sorbitan fatty acid esters, which are sold under the trade names Polysorbate or Tween.

Suitable ionic surfactants are selected from group of fatty acid salts, bile salts, phospholipides, phosphoric acid esters, carboxylates, sulphates, sulphonates and mixture thereof. A preferred ionic surfactant is sodium laurylsulphate.

The pharmaceutical composition according to the invention may comprise 0.1-10%, preferably 0.1-5% by weight of a surfactant.

Suitable mixing device in direct compression or optionally, wet granulation as described above is conventional equipment used for mixing of active ingredients, excipients or combination of active ingredient(s) and excipients. Conventional equipment is motionless (passive) mixers, fluidized beds, diffusion, biconic diffusion, biconic, turbula, cubic, planetary, Y-, V-shaped or high-shear mixer, drum etc. In the case of wet granulation as described above, the equipment is chosen from standard equipment for drying, i.e. fluid-bed dryer, plates, etc.

The solid dosage form may be, for example, immediate release dosage form, a fast melt dosage form, controlled release dosage form, lyophilized dosage form, delayed release dosage form, extended release dosage form, pulsatile release dosage form, mixed immediate release and controlled release dosage form, or a combination thereof. A solid dose form is preferably tablet formulation, which can be optionally coated. The solid dosage form is preferably an immediate release dosage form offering advantages regarding the bioavailability of the active compound.

If an immediate release dosage form is chosen, it will be clear for the skilled person that the amount of release controlling agent or agents, either individual or mixture thereof to be used in forming the outer portion will be determined based on various parameters such as the desired delivery properties, including the amount of active ingredient or substance to be delivered, the active ingredient or substance release rate desired, and the size of the micro matrix particles.

Pharmaceutical composition may consist of:
1-99%, preferably 5-50%, more preferably 5-15% by weight of olmesartan medoxomil,
1-99%, preferably 20-99%, more preferably 50-99% by weight of diluent,
1-90%, preferably 1-50% by weight of binder,
1-50%, preferably 2-40% by weight of disintegrant or superdisintegrant,
0.1-10% lubricant,
0.1-10%, preferably 0.1-5% by weight of surfactant, and optionally, 0.1 to 10% film coating layer.

The excipients present in the composition according to the invention can be diluents such as microcrystalline cellulose, powdered cellulose, lactose (anhydrous or monohydrate), compressible sugar, fructose, dextrates, other sugars such as mannitol, siliconised microcrystalline cellulose, calcium hydrogen phosphate, calcium carbonate, calcium lactate or combined diluents. Preferably, the excipients include at least one diluent selected from microcrystalline cellulose and lactose monohydrate.

The composition according to the invention may also comprise binders, such as povidone, microcrystalline cellulose, hydroxyethylcellulose, hydroxypropylcellulose, low-substituted hydroxypropylcellulose (comprising from 5 to 16% by weight of hydroxypropyl groups), hydroxypropylmethylcellulose or other cellulose ether, starch, pregelatinised starch or poly-methacrylate or mixture of binders. It is preferred that excipients include at least one binder selected from microcrystalline cellulose and low-substituted hydroxypropylcellulose.

Further, disintegrants and/or superdisintegrants may also be present such as starches (e.g. maize starch, potato starch), modified starches (sodium starch glycolate), modified cellulose (croscarmellose, i.e. cross-linked carboxymethylcellulose sodium), cross-linked polyvinyl-pyrrolidone (crospovidone), microcrystalline cellulose, carboxymethylcellulose sodium, Amberlite®, alginic acid, sodium alginate, guar gum, gellan gum, Xanthan SM®. If used as a disintegrant, microcrystalline cellulose is preferably used in an amount of 5 to 15% by weight. It is preferred that excipients include at least one disintegrant or superdisintegrant selected from croscarmellose, crospovidone and microcrystalline cellulose.

Further, lubricants may also be present as excipients, such as stearic acid, magnesium stearate, calcium stearate, sodium laurylsulphate, hydrogenated vegetable oil, hydrogenated castor oil, sodium stearyl fumarate, talc, macrogols. It is preferred that the excipients include at least one lubricant selected from magnesium stearate, talc and macrogols.

Excipients may have multiple functions, i.e. one excipient may be diluent and additionally binder, binder and disintegrant etc.

Optionally, the tablet cores may be coated with conventional materials used for film coating. Film coating formulations usually contain the following components: polymer(s), plasticizer(s), colourant(s)/opacifier(s), vehicle(s). In film coating suspension we can use minor quantities of flavours, surfactants and waxes. The vast majority of the polymers used in film coating are either cellulose derivatives, such as the cellulose ethers, or acrylic polymers and co-polymers. Occasionally encountered are high molecular weight polyethylene glycols, polyvinyl pyrrolidone, polyvinyl alcohol and waxy materials.

Typical cellulose ethers are hydroxyethylcellulose, hydroxypropylcellulose, hydroxypropyl-methylcellulose, methylcellulose. Acrylic polymers comprise a group of synthetic polymers with diverse functionalities. Some of them can be further modified to enhance swelling and permeability by the incorporation of materials such as water soluble cellulose ethers and starches in order to ensure complete disintegration/dissolution of the film.

The commonly used plasticizers may be categorized into three groups: polyols (glycerol, propylene glycol, macrogols), organic esters (phthalate esters, dibutyl sebacetate, citrate esters, triacetin), and oils/glycerides (castor oil, acetylated monoglycerides, fractionated coconut oil).

Colourants/opacifiers are classified into several groups: organic dyes and their lakes, inorganic colours, natural colours.

Combination of different materials form each group can be combined in defined ratio. Film coating suspensions can be used as ready-to-make preparations that are available on the market.

Film coating dispersion can be prepared by using different solvents such as water, alcohols, ketones, esters, chlorinated hydrocarbons, preferably water.

A composition of coating suspension (calculated on dry material) is particularly preferred which comprises:
1-99% by weight of polymer, preferably 1-95% of polymer,
1-50% by weight of plasticizer, preferably 1-40% of plasticizer,
0,1-20% of colourant/opacifier, preferably 0,1-10% of colourant/opacifier.

The immediate release dosage form may also include a material that improves the processing of the release controlling agents. Such materials are generally referred to as plasticizers. Preferred plasticizers include acetylated monoglycerides, butyl phthalyl butyl glycolate, dibutyl tartrate, diethyl phthalate, dimethyl phthalate, ethyl phthalyl ethyl glycolate, glycerin, ethylene glycol, propylene glycol, triethyl citrate, triacetin, tripropionin, diacetin, dibutyl phthalate, acetyl monoglyceride, polyethylene glycols, castor oil, triethyl citrate, polyhydric alcohols, acetate esters, glycerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, dioctyl phthalate, di-i-decyl phthalate, di-n-undecyl phthalate, di-n-tridecyl phthalate, tri-2-ethyl-hexyl trimellitate, di-2-ethylhexyl adipate, di-2-ethylhexyl sebacate, di-2-ethylhexyl azelate, dibutyl sebacate, glyceryl monocaprylate, glycerol distearate and glyceryl monocaprate.

Dissolution profiles were measured on a Dissolution tester ErwekaDT80 with an Agilent Diode Array Spectrophotometer 8453, in artificial gastric fluid, pH-value 2.0, spindle, 50 rev./min.

Preferably, the content uniformity is less than about 7.5%, preferably less than about 5% and more preferably less than about 5%. Most preferably the content uniformity is less than about 3%. The lower limit for the content uniformity is preferably zero. The content uniformity is determined by the corresponding USP test (Uniformity of dosage units, General Chapter 905, 2005), where 10 tablets are assayed individually, after which the arithmetic mean and relative standard deviation (RSD) are calculated. The USP criteria lie within 85-115% of the labelled claim, and the RSD is not greater than 6%.

Contents of olmesartan medoxomil in tablets are measured by HPLC, external standard method and UV detection are applied.

pH-values of a 20% (m/V) suspension of crushed tablets in water were determined by use of a calibrated pH-meter at a temperature between 20-25° C.

The present invention is illustrated by the following Examples without being limited thereto.

Melting points were taken on a Koffler melting point apparatus and IR spectra were taken on a Paragon 100 Perkin-Elmer FT-IR spectrometer.

EXAMPLES

Preparation of Olmesartan Medoxomil

Example 1

17.3 g (124.8 mmol) of $K_2CO_3$, 15 g (62.4 mmol) ethyl 4-(1-hydroxy-1-methylethyl)-2-propylimidazole-5-carboxylate (III) and 38.3 g (68.7 mmol) 4-[2-(trityltetrazol-5-yl)phenyl]-benzyl bromide (IVa) were suspended in 750 ml of acetonitrile. The suspension was then heated under reflux until the reaction was completed (7 h). 510 ml of acetonitrile were distilled off and the concentrate was cooled to 23 to 25° C. The mixture was stirred at this temperature overnight, then the suspension was cooled to 0° C. and stirred at this temperature for 1 h. The crude product (Va) was filtered off and washed 2× with 20 ml of cooled acetonitrile. Wet product was suspended in 450 ml of water, stirred for 1.5 h and after that filtered off. The mass of dried product (Va) was 39.5 g (89%). T=165-169° C.
IR: 1666, 1525, 1291, 1446, 1177, 881, 756, 699, 640

Example 2

36.0 g (50.3 mmol) ethyl 4-(1-hydroxy-1-methylethyl)-2-propyl-1-{4-[2-(trityltetrazol-5-yl)-phenyl]phenyl}-methyl imidazole-5-carboxylate (Va) and 3.0 g (75.4 mmol) of NaOH were suspended in 413 ml dimethylacetamide. The suspension was then stirred at room temperature for 20 h and after that 6.9 g (50.3 mmol) of $K_2CO_3$, were added. The mixture was cooled to 0° C. and solution of 15.4 g (70.4 mmol) 4-chloromethyl-5-methyl-2-oxo-1,3-dioxolene in 39 ml of dimethylacetamide were slowly added. The mixture was slowly heated to 50° C. and stirred at this temperature for 2 h. After esterification was completed, the mixture was cooled to 10° C. and poured into a mixture of 625 ml of ethyl acetate and 625 ml of 10% NaCl, and stirred at 25° C. for 15 min. The phases were separated and organic phase was washed 2× with 500 ml of 10% NaCl, dried over $Na_2SO_4$ and filtered. The filtrate was concentrated up to ½ (approximately 270 g) at reduced pressure.

To the resulting solution, 80 ml of ethanol and 8.3 ml (100 mmol) of conc. HCl were added and stirred at 24-26° C. for 3 h. To the cooled mixture 600 ml of water was added and pH of the suspension was estimated to 5 by addition of 5 M NaOH. The phases were stirred for 15 min and separated. Water phase was reextracted with 150 ml of ethyl acetate. Collected organic phases were dried over $Na_2SO_4$, filtered and concentrated under reduced pressure. 560 ml of ethyl acetate were added and the mixture was evaporated again. After that, 300 ml of ethyl acetate were added and the mixture was cooled to 20° C. and stirred for 1 h, filtered off and washed with 20 ml of fresh ethyl acetate. The yield of the product (I) was 21 g (75%).

Crystallization of Olmesartan Medoxomil:

Example 3

1.11 g of olmesartan medoxomil was dissolved in 12.5 ml of 2-butanone at reflux temperature. The solution was slowly cooled to room temperature and stirred at this temperature for 20 h. During this process olmesartan medoxomil was slowly crystallized. The product was filtered and dried for 18 h at room conditions. We obtained 0.98 g of olmesartan medoxomil.

The crystalline form of the product was the same as described in *Annual Report of Sankyo Research Laboratories Vol.* 55 (2003).

Example 4

1.2 g of olmesartan medoxomil was dissolved in 8.5 ml of 2-butanone at reflux temperature. The solution was slowly cooled to room temperature and stirred at this temperature for 20 h. During this process olmesartan medoxomil was slowly crystallized. The suspension was then cooled to 0° C. and stirred at this temperature for 2 h. The product was filtered and dried under reduced pressure at 30-40° C. for 3 h. We obtained 0.98 g of olmesartan medoxomil. The crystalline form of the product was the same as described in *Annual Report of Sankyo Research Laboratories Vol.* 55 (2003).

Example 5

0.5 g of olmesartan medoxomil was dissolved in 4 ml of isobutanol at reflux temperature. The solution was slowly cooled to 0° C. and stirred at this temperature for 3 h. During this process olmesartan medoxomil was slowly crystallized. The product was filtered and dried for 18 h at room conditions. We obtained a crystalline form of olmesartan medoxomil (0.45 g), which is a new polymorph form. The X-ray diffraction pattern shows peaks at 7.4, 9.0, 9.6, 11.6, 12.0, 13.4, 16.0, 17.9, 21.1±0.2 degrees 2-theta. X-ray powder diffraction patterns were obtained by Phillips PW3040/60 X'Pert PRO powder diffractometer; CuKα radiation 1.541874 Å, 3°<2θ<20<31°.
T=182-184° C.

Example 6

2 g of olmesartan medoxomil was dissolved in 30 ml of THF at reflux temperature. The solvent was slowly evaporated at reduced pressure to dry residue. During this process olmesartan medoxomil was slowly crystallized. The product was collected and dried for 18 h at room conditions. We obtained crystalline form of olmesartan medoxomil (1.86 g). T=182-184° C.

Example 7

0.5 g of olmesartan medoxomil was dissolved in 18 ml of methylene chloride at reflux temperature. The solvent was slowly evaporated at reduced pressure to dry residue. We obtained amorphous form of olmesartan medoxomil (0.43 g).

Example 8

2 g of olmesartan medoxomil was dissolved in 20 ml of heptane at reflux temperature. The solution was slowly cooled to room temperature and stirred at this temperature for 3 h. During this process olmesartan medoxomil was slowly precipitated. The product was filtered and dried for 18 h at room conditions. We obtained amorphous form of olmesartan medoxomil (0.45 g).
T=120-140° C.

Example 9

2 g of olmesartan medoxomil was dissolved in 45 ml of isopropanol at reflux temperature. The solution was slowly cooled to room temperature and stirred at this temperature for 3 h. During this process olmesartan medoxomil was slowly precipitated. The product was filtered and dried for 18 h at room conditions. We obtained 1.96 g of olmesartan medoxomil.
Average particle size: 40 μm
The crystalline form of the product was the same as described in *Annual Report of Sankyo Research Laboratories Vol.* 55 (2003)

Example 10

1.1 g of olmesartan medoxomil was dissolved in 15 ml of acetone at reflux temperature. The solution was concentrated at reduced pressure to approximately ½ of the starting volume. The concentrate was cooled to 0° C., filtered and dried. 0.9 g of olmesartan medoxomil was isolated.
The crystalline form of the product was the same as described in *Annual Report of Sankyo Research Laboratories Vol.* 55 (2003).

Example 11

12 g of olmesartan medoxomil was dissolved in 174 ml of ethanol at reflux temperature. The solution was slowly cooled to room temperature without stirring. The mixture was left at room temperature overnight (18 h). The product was filtered and dried for 3 h in vacuum drier for 3 h. We obtained 7.3 g of olmesartan medoxomil.
Average particle size: 253 μm
The crystalline form of the product was the same as described in *Annual Report of Sankyo Research Laboratories Vol.* 55 (2003)
Pharmaceutical Formulation of Olmesartan Medoxomil

Example 12

40 g of olmesartan medoxomil, 104 g of microcrystalline cellulose, 230 g of lactose monohydrate and 40 g of low-substituted hydroxypropylcellulose are homogenised. Finally, 6 g of magnesium stearate is admixed to prepare compressing mixture. Compressing mixture is compressed to cores with theoretical weight 210 mg.
Cores were coated with film coating suspension, containing (calculated per dry part of film-coating suspension) hydroxypropylcellulose (43.75% by weight), hydroxypropylcellulose (37.5% by weight), talc (6.25% by weight) and titanium dioxide (12.5% by weight). Theoretical weight of film coated tablet is 218 mg.

Example 13

Cores of Example 1 are coated with ready-to-make film coating suspension, containing (calculated per dry part of film-coating suspension) partially hydrolyzed polyvinyl alcohol (40% by weight), titanium dioxide (25% by weight), macrogol (20.2% by weight) and talc (14.8% by weight). Theoretical weight of film coated tablet is 218 mg.

Example 14

52 g of microcrystalline cellulose, 114 of lactose monohydrate, 20 g of low-substituted hydroxypropylcellulose and 2 g sodium laurylsulfate are homogenised and sprayed with purified water in fluid-bed granulator. Granulate is sieved. 40 g of olmesartan medoxomil, 52 of microcrystalline cellulose, 114 g of lactose monohydrate and 20 g of low-substituted hydroxypropylcellulose are added to the granulate and mixed. Finally, 6 g of magnesium stearate is admixed to prepare compressing mixture. Compressing mixture is compressed to cores with theoretical weight 210 mg.
Cores are coated with coating suspension of Example 12 or 13.

Examples 15a-22a

Preparation of Compression Mixture

Components (1-5) are homogenised in a high-shear mixer. Finally, magnesium stearate (6) is admixed to obtain the compression mixture. Particle size (i.e. average particle size, 10% particles below defined size, 10% of particles above defined size, 50% of particles above defined size) of active ingredient (olmesartan medoxomil) refers to volume particle diameter, determined by laser light scattering of a sample comprising 100-800 mg of active ingredient dispersed in 5-8 ml of vegetable oil (i.e. sunflower oil) and not containing any solubilizers or surfactants, using a NMalvern Mastersizer instrument MS2000. Loss on drying of compression mixture was measured using a Mettler Toledo HR73 halogen moisture analyzer at 85° C. for 20 minutes. The results are shown in Table 1. Different types of microcrystalline cellulose (2) were used. Furthermore, different types of lactose monohydrate (3) were used in different Examples.

TABLE 1

| Components (g) | 15a | 16a | 17a | 18a | 19a | 20a | 21a | 22a |
|---|---|---|---|---|---|---|---|---|
| 1 Olmesartan medoxomil | 40.00[a] | 40.00[a] | 40.00[a] | 40.00[a] | 40.00[a] | 40.00[a] | 40.00[a] | 40.00[b] |
| 2 Microcrystalline cellulose (Avicel PH 102) | 104.00 | 104.00 | 104.00 | 104.00 | 104.00 | 104.00 | — | 104.00 |
| Microcrystalline cellulose (Avicel PH 112) | — | — | — | — | — | — | 104.00 | — |
| 3 Lactose monohydrate (Pharmatose DCL 14) | 230.00 | — | — | — | — | — | — | — |
| Lactose monohydrate (Pharmatose DCL 15) | — | 226.60 | 229.00 | 228.60 | 230.00 | — | 230.00 | 230.00 |
| Tablettose | — | — | — | — | — | 230.00 | — | — |
| 4 LH-11[1] | 40.00 | 40.00 | 40.00 | 40.00 | 40.00 | 40.00 | 40.00 | 40.00 |
| 5 Ascorbic acid | — | 3.40 | — | — | — | — | — | — |
| Anhydrous citric acid | — | — | 1.00 | — | — | — | — | — |
| Tartaric acid | — | — | — | 1.40 | — | — | — | — |
| 6 Magnesium stearate | 6.00 | 6.00 | 6.00 | 6.00 | 6.00 | 6.00 | 6.00 | 6.00 |
| Loss on drying of compression mixture (%) | 1.86 | 1.57 | 1.81 | 2.08 | 1.97 | 2.21 | 2.05 | 2.10 |

[a] Active ingredient with average particle size 8 μm, 10% of particles below 1.2 μm, 10% of particles above 7.2 μm, 50% of particles above 16.8 μm
[b] Active ingredient with average particle size 4 μm, 10% of particles below 0.7 μm, 10% of particles above 2.6 μm, 50% of particles above 7.3 μm
LH-11[1] Commercially available low-substituted hydroxypropylcellulose Examples 15b-22b Tablet Cores Preparation Compression mixtures (15a-22a) were compressed using into round tablet cores (1b-8b) with a theoretical weight 210 mg on automatic rotary compressing mixture with defined main pressure. The hardness of the compressed tablets cores and the disintegration time (in minutes) thereof in purified water at 37° C. were measured according to Ph.Eur. Friability of all samples was below 1%. The results are shown in Table 2.

TABLE 2

|  | 15b | 16b | 17b | 18b | 19b | 20b | 21b | 22b |
|---|---|---|---|---|---|---|---|---|
| Weight (mg) | 210 | 210 | 210 | 210 | 210 | 210 | 210 | 210 |
| Main pressure (kN) | 6.7 | 7.9 | 8.0 | 7.7 | 8.3 | 8.4 | 8.0 | 6.0 |
| Hardness (N) | 85-113 | 89-111 | 98-118 | 86-108 | 106-124 | 87-105 | 83-103 | 88-118 |
| Disintegration time (min) | 3-3.5 | 1-1.5 | 1-1.5 | 1-1.5 | 1.5 | 0.5 | 1 | 2.5-3 |

In addition, the compressed tablet cores (15b-22b) were coated in an automatic coating pan with water-based film coating suspension of a ready-to-make mixture, commercially available as Opadry F28751 II HP white. The theoretical weight of the coated tablets containing the tablet cores (1b-8b) was 218 mg. pH values and content of active ingredient in film coated tablets are collected in Table 3.

TABLE 3

|  | 15b | 16b | 17b | 18b | 19b | 20b | 21b | 22b |
|---|---|---|---|---|---|---|---|---|
| pH | 6.85 | 4.66 | 6.27 | 4.94 | 6.86 | 6.88 | 6.85 | 6.87 |
| Content of active ingredient (%) | 96.6 | 99.8 | 100.5 | 99.6 | 100.0 | 99.4 | 97.9 | 99.8 |

Example 23

Tablets of composition of Example 15 were prepared with the use of olmesartan medoxomil with different particle size: average particle size 34 μm, 10% of particles below 13.1 μm, 10% of particles above 60.0 μm, 50% of particles above 30.3 μm. A significant difference was observed in solubility of olmesartan medoxomil in acidic media, used in Examples 15 and 22, where active ingredient used in Example 15 is preferred and results in better bioavailability if compared to composition of Example 22.

The invention claimed is:

1. A process for the preparation of olmesartan medoxomil which comprises:
   (i) alkylating ethyl 4-(1-hydroxy-1-methylethyl)-2-propylimidazole-5-carboxylate (III) with 4-[2-(trityltetrazol-5-yl)phenyl]-benzyl bromide (IVa) or 4'-bromomethyl-biphenyl-2-carbonitrile (IVb) in acetonitrile and in the presence of a base to yield a reaction suspension;
   (ii) crystallizing and filtering the reaction suspension, wherein acetonitrile is also used as a crystallization solvent, to obtain an ethyl ester of formula (V); and
   (iii) converting the ethyl ester of formula (V) to olmesartan medoxomil in a one pot process comprising:
       (a) hydrolyzing the ethyl ester of formula (V),
       (b) esterifying with a 4-substituted methyl-5-methyl-2-oxo-1,3-dioxolene (VI), and
       (c) subsequently deprotecting a trityl protection group.

2. The process according to claim 1, wherein the acetonitrile, which is used as a reaction and crystallization solvent, is partially distilled off.

3. The process according to claims 1, wherein the product of the alkylation reaction between ethyl 4-(1-hydroxy-1-methylethyl)-2-propylimidazole-5-carboxy late (II) and 4-[2-(trityltetrazol-5-yl)phenyl]-benzyl bromide (IVa) or 4'-bromomethylbiphenyl-2-carbonitrile (IVb) is crystallized from the reaction mixture.

4. The process according to claim 1, wherein the product of the alkylation reaction between ethyl 4-(1-hydroxy-1-methylethyl)-2-propylimidazole-5-carboxylate (III) and 4-[2-(trityltetrazol-5-yl)phenyl]-benzyl bromide (IVa) or 4'-bromomethylbiphenyl-2-carbonitrile (IVb) is, after crystallizing and filtering, suspended in water and recrystallized from acetonitrile.

5. The process according to claim 1, wherein, when the alkylation step is performed with 4'-bromomethylbiphenyl-2-carbonitrile (IVb), comprises the step of: performing a cycloaddition reaction leading to the tetrazole moiety, said reaction is performed before or after the hydrolysis of the ethyl ester and the esterification with a 4-substituted methyl-5-methyl-2-oxo-1,3-dioxolene derivative (VI).

6. The process according claim 1, wherein the base used is potassium carbonate.

7. The process of claim 1, wherein said 4-substituted methyl-5-methyl-2-oxo-1,3-dioxolene (VI) is 4-chloromethyl-5-methyl-2-oxo-1,3-dioxolene.

8. The process according to claim 1, wherein the alkylation step of ethyl 4-(1-hydroxy-1-methylethyl)-2-propylimidazole-5-carboxylate (III) with 4-[2-(trityltetrazol-5-yl)phenyl] benzyl bromide (IVa) is performed in the presence of potassium carbonate as base.

9. The process according to claim 1, wherein the hydrolysis of the ethyl ester of formula (V), and the esterification with 4-substituted methyl-5-methyl-2-oxo-1,3-dioxolene (VI) are carried out in dimethylacetamide.

10. The process according to claim 1, wherein the deprotection of the trityl protection group from trityl olmesartan medoxomil is carried out in the presence of an acid selected from organic acid, inorganic acid, their derivatives, and mixtures thereof, and a co-solvent.

11. The process according to claim 10, wherein the co-solvent is selected from the group consisting of alcohols, ketones, nitriles and water.

12. The process according to claim 11, wherein the concentration of the co-solvent is up to 30% (v/v).

13. The process according to claim 10, wherein the deprotection of the trityl protection group from trityl olmesartan medoxomil is carried out in ethyl acetate and in the presence of hydrochloric acid.

14. The process of claim 13, wherein after the deprotection of the trityl protection group in ethyl acetate is completed, the reaction mixture is cooled and neutralized with an aqueous solution of an inorganic base to a pH value up to 6, and the product is isolated.

15. The process of claim 14, wherein after the deprotection of the trityl protection group in ethyl acetate is completed, the reaction mixture is cooled to room temperature.

16. The process according to claim 14, wherein the solvent phases are separated, wherein the water phase is re-extracted with an organic solvent, preferably ethyl acetate, the collected organic phases are concentrated and cooled, and the precipitated olmesartan medoxomil is isolated.

17. The process according to claim 14 wherein trityl alcohol remains dissolved in the reaction mixture and does not precipitate.

18. The process according to claim 1, wherein the reaction mixture after deprotection is neutralized up to pH 6.

* * * * *

UNITED STATES PATENT AND TRADEMARK OFFICE
CERTIFICATE OF CORRECTION

PATENT NO. : 7,943,779 B2  Page 1 of 1
APPLICATION NO. : 11/997133
DATED : May 17, 2011
INVENTOR(S) : Zupancic et al.

It is certified that error appears in the above-identified patent and that said Letters Patent is hereby corrected as shown below:

At column 21, line 24 (approx), in Claim 3, change "claims" to --claim--.

At column 21, line 26 (approx), in Claim 3, change "carboxy late" to --carboxylate--.

At column 21, line 45 (approx), in Claim 6, change "according" to --according to--.

Signed and Sealed this
Twenty-ninth Day of November, 2011

David J. Kappos
*Director of the United States Patent and Trademark Office*